United States Patent [19]
Klein

[11] Patent Number: 5,707,602
[45] Date of Patent: Jan. 13, 1998

[54] MEASUREMENT OF GASTRIC EMPTYING

[75] Inventor: Peter D. Klein, Houston, Tex.

[73] Assignee: Meretek Diagnostics, Houston, Tex.

[21] Appl. No.: 619,140

[22] Filed: Mar. 25, 1996

[51] Int. Cl.$^6$ .................. A61K 51/00; A61M 36/14
[52] U.S. Cl. .................. 424/1.17; 424/1.81; 424/439
[58] Field of Search .................. 424/1.11, 1.17, 424/1.37, 1.65, 1.69, 1.81, 9.1, 9.2, 400, 439; 426/282, 283, 531, 549, 653; 435/257.1, 243; 47/1.4

[56] References Cited

U.S. PATENT DOCUMENTS

| 4,897,266 | 1/1990 | Herve et al. | 424/195.1 |
| 5,140,993 | 8/1992 | Opekun, Jr. et al. | 128/730 |
| 5,164,308 | 11/1992 | Kyle | 47/1.4 |
| 5,466,434 | 11/1995 | Kyle | 424/9.1 |

OTHER PUBLICATIONS

Maes et al (1996), Gut, vol. 38, pp. 23–27, "Relation between Gastric Emptying Rate and Rate of Intraluminal Lipolysis".

Maes et al (1995), Gut, vol. 36, pp. 183–188, "Relation between Gastric Emptying Rate and Energy Intake in Children Compared with Adults".

Braden et al (1995), Gastroenterology, vol. 108, pp. 1048–1055, "The [$^{13}$C] Acetate Breath Test Accurately Reflects Gastric Emptying of Liquids in Both Liquid and Semisolid Test Meals".

Maes et al (1994), J. Nucl. Med., vol. 35, pp. 824–831, "Combined Carbon–13–Glycinol Carbon–14–Octanoic Acid Breath Test to Monitor Gastric Empty Rates of Liquids and Solids".

Maes et al (1995), Aliment Pharmacol. Ther., vol. 9, pp. 11–18, "Influence of Actreotide on the Gastric Emptying of Solids and Liquids in Normal Healthy Subjects".

*Primary Examiner*—John Kight
*Assistant Examiner*—Dameron L. Jones
*Attorney, Agent, or Firm*—Bush, Riddle & Jackson

[57] ABSTRACT

A biscuit adapted to be ingested by a patient to enable measurement of gastric emptying has added prior to baking Spirulina Platensis alga grown in a $^{13}CO_2$ atmosphere. These single cell organisms are oxidized after digestion in the small intestine to produce a detectible rise in level of $^{13}CO_2$ in the patient's breath which is sampled and plotted to enable diagnosis of abnormal gastric emptying rates.

9 Claims, 1 Drawing Sheet

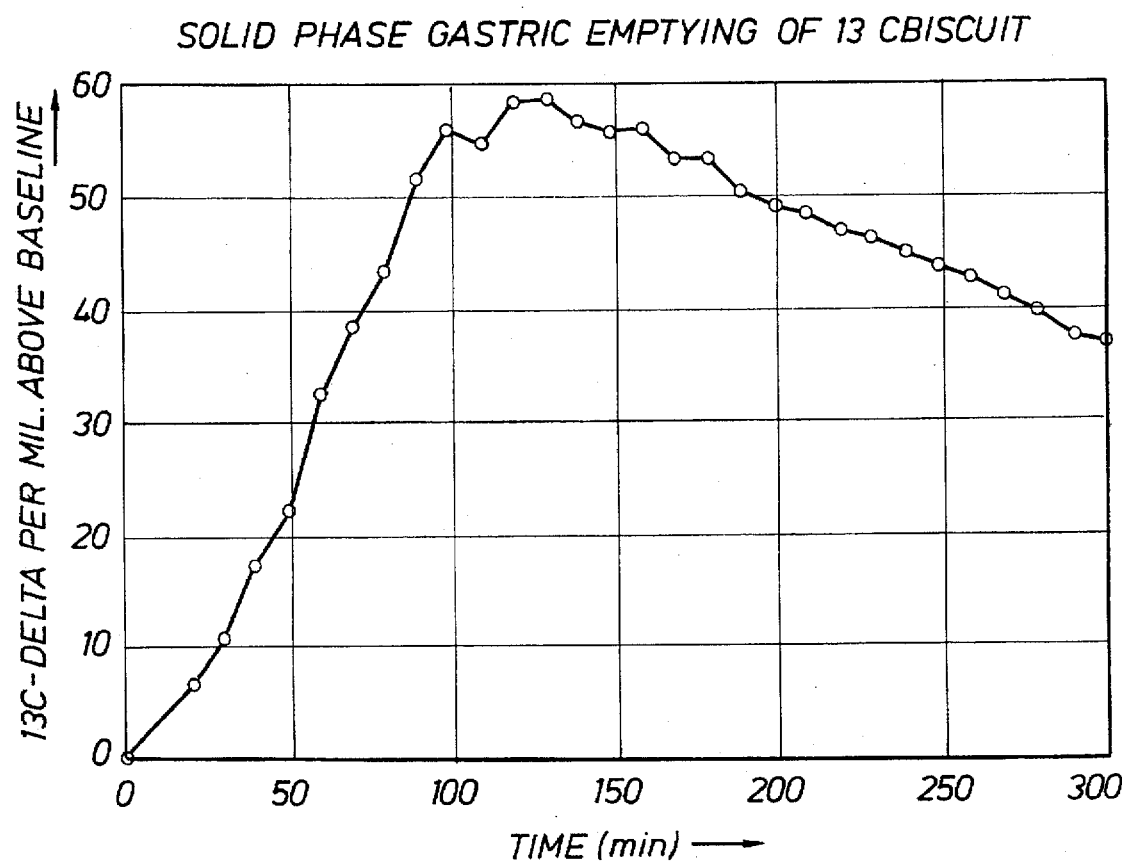

MEASUREMENT OF GASTRIC EMPTYING

FIELD OF THE INVENTION

This invention relates generally to diagnosis of gastrointestinal disorders in humans, and particularly the rate at which food being digested in the stomach is emptied into the small intestine in order to determine abnormal delay or dumping.

BACKGROUND OF THE INVENTION

Digestion of all foods in humans begins in the stomach where both solid and liquid matter is mixed with gastric juices that are secreted by the stomach walls. The gastric juice is predominately hydrochloric acid, but also includes enzymes that break down food constituents so that they can be absorbed and used. The contents of the stomach are emptied into the small intestine via the pyloric sphincter which opens and closes to release pulses of the mixed solids and liquids. The rate of such emptying is regulated by this sphincter, and is more rapid in the case of liquids than solids. In both cases the rate is determined by the calorie content of the meal. The higher the calorie content, the lower the rate of discharge. In addition, the solid phase of the food must undergo comminution, or reduction in particle size, which is caused by contractions of the stomach walls until a particle size of about 1 mm in diameter is attained.

A disorder in the rate of gastric emptying can result either in too rapid or in delayed emptying. When the rate is accelerated the food is "dumped" into the small intestine prematurely. When delayed, the time required to empty the stomach is excessive. Delayed gastric emptying often is encountered in diabetic patents and may be associated with abdominal pain, cramping and bloating. Although some medications have been developed to increase gastric emptying, their efficacy is still under investigation.

At present, diagnosis and measurement of gastric emptying is possible only at highly specialized nuclear medicine facilities. Testing requires use of one radioactive tracer for the liquid phase and a second radioactive tracer for the solid phase. Movement of such tracers is monitored by positioning a recumbent patient between two large gamma ray responsive scintillation counters which measure the position and quantity of each isotype from the from to the back of the patient. This procedure takes 3 to 9 hours to perform.

If the tracer is totally soluble in the liquid phase, its introduction poses no particular problem because the tracer then is miscible with the gastric juices and is emptied from the stomach along with the movement of the liquid phase. But introduction of the radioactive tracer into the solid phase is more difficult because it must be attached to the protein in a manner such that it is not leached out by gastric juices, but cleaves to individual particles which leave the stomach. Eventually the tracer is lost when the food particles undergo enzymic digestion in the small intestine. One method involves "sizzling" the isotype with a chicken liver puree and mixing the semi-solid food mass with a snack can of beef stew.

Recently, alternative liquid and solid phase tracers have been proposed. These tracers are $^{13}C$ labeled molecules which, when absorbed from the intestine, are rapidly oxidized to carbon dioxide ($CO_2$). The oxidation can be detected from an increase in the concentration of $^{13}C$ $CO_2$ in the breath. These tracers have the advantages that they are nonradioactive and do not expose the patient to harmful rays, and that breath sampling does not involve an invasive procedure. For example, sodium 1-$^{13}$C- acetate has been used as a liquid-phase marker, and the appearance of labeled $CO_2$ after marker administration in a liquid meal has been correlated with the emptying of a radioactive liquid phase marker that is administered simultaneously. For the solid food phase, the markers 1-$^{13}$C-octanoic acid has been proposed. This acid is added to a raw egg yolk, which is microwaved. The egg white is cooked separately, and the two are combined in an egg sandwich which is ingested by the patient.

The use of the above non-radioactive substrates has been validated against the prior radiological methods with acceptable correlation. Regardless of which type of tracer is used, solid-phase emptying measurements are more clinically useful than those for liquid-phase emptying. Problems still exist, however, in the use of either of the solid-phase markers because both require that the exogenous substance be added and attached to the test meal. When technitium-labeled serum albumin colloid is used, the metal ion is bound to the protein; when octanoic acid is used, the fatty acid is dissolved in the lipid phase of the egg yolk lipoprotein. Both labeling processes require that the physician prepare and cook the meal before the test administration. The nature of such a procedure makes the development of a standard solid-phase emptying protocol or procedure difficult, and hinders the commercial development of an office-based procedure.

The general object of the present invention is to provide a new and improved measurement technique for determining gastric emptying in a more reliable, safe and accurate manner.

Another object of the present invention is to provide a new and improved technique for diagnosing disorders in gastric emptying through use of intrinsically labeled organisms as markers for solid-phase meals.

SUMMARY OF THE INVENTION

These and other objects are attained in accordance with the concepts of the present invention through the provision of a method and means for measuring gastric emptying which employs intrinsically labeled single cell organisms as markers for solid-phase meals. The intrinsically labeled single cell marker organisms, proteins, lipids or carbohydrates are incorporated into a baked product that is ingested by the patient. The product containing the marker organisms preferably is a biscuit having an edible photosynthetic alga therein, such as Spirulina Platensis which has been grown in an atmosphere of about 99% $^{13}CO_2$. The biscuit, having a unique composition including the alga, preferably is packaged with a fat-containing spread and a small serving of a fruit juice. After fasting for a period of time so that a breath sample can be collected which establishes a baseline measurement, the patient consumes the biscuit with the spread and the juice, after which breath samples are collected at approximately 10 minute intervals over a period of several hours. The $^{13}CO_2$ content data of these samples is compared to the base line data for analysis and calculation of gastric emptying time, from which a diagnosis of abnormal typing can be made.

BRIEF DESCRIPTION OF THE DRAWINGS

The present invention has the above as well as other objects, features and advantages which will become more clearly apparent in connection with the following detailed description of a preferred embodiment, taken in conjunction with the appended drawing in which:

The drawing Figure is a graph showing change of concentration of $^{13}C$ in breath samples vs. time to illustrate this invention.

DETAILED DESCRIPTION OF A PREFERRED EMBODIMENT

In accordance with the present invention, the solid food to be chewed and swallowed to initiate a gastric emptying test is in the form of an edible biscuit made from a dough recipe and having about 150 calories. The biscuit contains carbohydrates, protein, fat and an mount of $_{13}C$ Spirulina which provides a unique combination of ingredients. The alga is photosynthetic and is grown in an atmosphere of about 99% $^{13}CO_2$, so that as a consequence of the photosynthetic process all carbon atoms contained in the alga are $^{13}C$. Spirulina platensis is a single celled organism and the quantity required to produce a detectable test signal is small. The alga is incorporated into the dough mixture before baking. The biscuit of the present invention preferably is packaged with an individual portion of cream cheese, peanut butter or other fat-containing spread, plus a small portion of a fruit juice to bring the total caloric value of the meal to about 300.

A recipe by which four (4) of the biscuits in accordance with this invention can be made has the following ingredients:

100 g. wheat flour 50 g. rye flour 90 ml. cold coffee 10 g. molasses 3 g. dried yeast 4 g. salt 4 g. anise seeds 2 g, dry uniformly $^{13}C$ - labeled Spirulina platensis The above ingredients are prepared by sifting the Spirulina together with the wheat and rye flours, and in a one quart metal bowl dissolving the molasses in the coffee, and adding the yeast, salt and anise seeds. The flour then is added stepwise to the liquid and worked into a dough ball. The dough ball is kneaded for about 5 minutes and then divided into 4 equal pieces, which are rolled out, balls and placed in a non-stick pan. The balls are flattened into round rolls which are allowed to rise in a warm location for about 45 minutes. The rolls are baked in an oven preheated to 325° F. for about 25 minutes, and then are stored in individual pint-size freezer bags and cooled in a freezer at −20° F. until needed for use.

To perform a gastric emptying test, the patient fasts overnight, and the next morning a baseline sample of breath is collected using the apparatus disclosed and claimed in the Opekun-Klein breath collection U.S. Pat. No. 5,140,993, issued Aug. 25, 1992 which is incorporated herein by reference. The sample is transferred to an evacuated test tube in the kit, and then analyzed to obtain a baseline carbonate level. The patient then spreads the cheese or other substance on a biscuit and ingests it, together with the fruit juice. Breath samples then are taken using the above-mentioned system, and are collected at about 10-minute intervals over the succeeding 4 hours or so. The samples are analyzed to obtain data points for a graph as shown in the drawing Figure, which has change in concentration of $^{13}C$ in respiratory $CO_2$ as the ordinate and elapsed time as the abscissa. Beyond the uppermost data points where the change values have begun to decline, the curve will decrease exponentially to the baseline. The graph enables a calculation of gastric emptying time or rate, so that the results can be reported to the physician. The drawing Figure shows the curve and its general shape in the case where emptying time is normal. Deviation therefrom indicates a gastric emptying disorder.

It now will be recognized that a new and improved non-invasive and radiation-free method and means has been disclosed for measuring gastric emptying for diagnostic purposes. Certain changes and modifications may be made in the disclosed embodiment without departing from the inventive concepts involved. For example, a $^{14}C$ labeled molecule could be used, although $^{13}C$ is preferred. Thus, it is the aim of the appended claims to cover all such changes and modifications falling within the true spirit and scope of the present invention.

What is claimed is:

1. A method of measuring gastric emptying time comprising the steps of: preparing a biscuit containing an edible photosynthetic alga labeled with a carbon isotope, having a patient ingest said biscuit so that the carbon labeled nutrients therein are absorbed in the small intestine and oxidized to labeled $CO_2$; and detecting the level of $CO_2$ in breath samples taken from the patient at periodic intervals to determine the rate of gastric emptying.

2. The method of claim 1 wherein said alga is Spirulina platensis which has been grown in an atmosphere of $^NCO_2$ where N is one of the numbers 13 and 14.

3. The method of claim 2 wherein said biscuit is made from a dough recipe containing specifically labeled $^NC$ carbohydrates, protein, and fat, and where N is one of the numbers 13 and 14.

4. The method of claim 3 where prior to ingestion the biscuit is provided with a fat-containing spread.

5. A food adapted to be ingested by a patient in connection with a gastric emptying test, comprising: a biscuit having added thereto prior to baking photosynthetic single cell organisms grown in an atmosphere high in $^NCO_2$ so that when oxidized a detectible rise in the $^NCO_2$ content of the patient's breath is produced, N being one of the numbers 13 and 14.

6. The food of claim 5 where the organisms are an edible alga.

7. The food of claim 6 wherein said alga is Spirulina Platensis.

8. The food of claim 7 wherein said biscuit contains uniformly labeled carbohydrates, protein and fats to give it a calorie value of about 150.

9. The food of claim 8 further including a fat-containing spread placed on said biscuit prior to ingestion.

* * * * *